(12) United States Patent
Beckers et al.

(10) Patent No.: US 7,756,248 B2
(45) Date of Patent: Jul. 13, 2010

(54) X-RAY DETECTION IN PACKAGING

(75) Inventors: Detlef Beckers, Nordhorn (DE);
Vladimir Kogan, Enschede (NL); Jorg Bolze, Almelo (NL); Christian W. Lehmann, Mulheim (DE); Harald G. Schweim, Cologne (DE); Klaus-Jurgen Steffens, Rheimbach (DE)

(73) Assignee: Panalytical B.V., Almelo (NL)

( * ) Notice: Subject to any disclaimer, the term of this patent is extended or adjusted under 35 U.S.C. 154(b) by 0 days.

(21) Appl. No.: 12/370,540

(22) Filed: Feb. 12, 2009

(65) Prior Publication Data

US 2009/0232276 A1 Sep. 17, 2009

(30) Foreign Application Priority Data

Feb. 15, 2008 (EP) .................................. 08151542

(51) Int. Cl.
G01N 23/06 (2006.01)
G01N 23/20 (2006.01)
G01N 23/04 (2006.01)

(52) U.S. Cl. ............................... 378/53; 378/71; 378/57
(58) Field of Classification Search ............. 378/51–57, 378/70–75, 81
See application file for complete search history.

(56) References Cited

U.S. PATENT DOCUMENTS 6,324,253 B1 11/2001 Yuyama et al.
6,347,131 B1 * 2/2002 Gusterson .................... 378/54

OTHER PUBLICATIONS

Anibou, Noureddine, et al., "EDXRD Probe for Pharmaceutical Verification," XP-002486175. XStream Systems, Inc, Sebastian, FL, 2007 (1 page).
Anibou, Noureddine, et al., "EDXRD Probe for Pharmaceutical Verification," XP-002486176. XStream Systems Inc, Orlando, Fl, 2008, (20 pages).
Maurin, Jan K., et al., "The Usefulness of Simple X-Ray Powder Diffraction Analysis for Counterfeit Control—The Viagra(r) Example," XP-005901678. *Journal of Pharmaceutical and Biomedical Analysis*, No. 43, 2007, (pp. 1514-1518).
Kogan, V.A., et al., "XRPD for Nondestructive Characterization of Solid Dosage Forms," XP-002486177. DANNALAB, Enschede, The Netherlands & PANalytical B.V., Almelo, The Netherlands, 2006 (1 page).
Kogan, V.A., et al., "Advanced XRPD System for the Characterization of Pharmaceutical Compounds," Pharmaceutical Powder X-ray Diffraction Symposium (PPXRD), 2006.

(Continued)

*Primary Examiner*—Irakli Kiknadze
(74) *Attorney, Agent, or Firm*—Blakely, Sokoloff, Taylor & Zafman LLP

(57) ABSTRACT

Angle dispersive X-ray diffraction is used to test pharmaceutical products including a dosage form inside packaging, for example a tablet inside a blister pack, without removing the dosage form from the packaging. The dosage form is aligned with a measurement system having an X-ray source for generating X-rays, X-ray optics, and an X-ray detector for detection of X-rays. Then, at least one X-ray signature is measured on a predetermined location on the dosage form. The measured X-ray signature is compared with reference X-ray signatures in a data library.

18 Claims, 7 Drawing Sheets

OTHER PUBLICATIONS

Kogan, V.A., et al.. "Characterization of formulations and drug products by PXRD," International Workshop on Physical Characterization of Pharmaceutical Solids (IWPCPS), 2007.

Kogan, V.A., et al., "XRPD for Nondestructive Characterization of Solid Dosage Forms," Pharmaceutical Powder X-ray Diffraction Symposium (PPXRD), 2007.

* cited by examiner

X-RAY DETECTION IN PACKAGING

FIELD OF INVENTION

The invention relates to X-ray Detection, in particular using X-ray Diffraction of packaged products, such as pharmaceuticals.

RELATED ART

Pharmaceutical dosage forms typically include an active pharmaceutical ingredient (API), an excipient, and optional coatings. The API may be crystalline, usually employed in delayed release drugs, or amorphous, often employed in faster release drugs. The drug can also be in the form of lyophilised amorphous powder, having a low density, such as vaccines. The dosage form may be solid, powder, granules, microtablets, liquid or gel.

A pharmaceutical product includes one or more drug dosage forms inside packaging. Most commonly, the packaging is blister packaging, but bottles, vials and other carriers are also possible. Blister material is usually aluminium or polymer, and for other packaging it may be polymers or glass. Such inner packaging is normally then contained inside outer packaging, for example a cardboard box, together with additional information.

The problem of fake drugs is increasing—a growing number of fake drug products are entering the sales channels. Unfortunately, this means that the contents of the packaging may include no pharmaceutical product, different excipients or indeed completely new substances from what is specified.

Unfortunately, it is not possible to routinely test drugs since to open the inner packaging and remove the drug for testing would mean that the drug product could not be delivered to the customer. Thus, it is not presently practicable to check drugs, for example at a customs border post.

There is accordingly a need to check the exact identity of a drug product without opening the inner packaging.

For producers of fake drugs, the main goal is to make money. There are a number of different levels of sophistication involved.

At the low end, the drug content may be completely fake. This however is dangerous to the vendor as the absence of therapeutic results is frequently obvious to a purchaser. Such low end fakes are only likely therefore in an unregulated market with many small buyers and resellers or perhaps via internet sales.

Low end fakes may include no relevant API, a substituted excipient, and a coating designed purely to be of the correct colour.

At an intermediate level, the fake drugs may include some form of API, often a cheap substitute with some form of pharmaceutical effect. However, the crystallinity of the API may well not be correct, particularly when the real drug has an amorphous API. The excipient may be correct or substituted. Again, the coating will be chosen to reproduce the colour. Such intermediate level fakes will use realistic packaging and labelling, but may not be exact.

High end fakes attempt to reproduce the dosage form as much as possible. For these fakes, much effort goes into exact reproduction of packaging and fake documentation. However, the dosage form itself is designed to withstand occasional checks and to produce some therapeutic effect. Thus, the API will normally be correct, possibly with the wrong crystallinity. High-end fakes are a particular problem for developed markets, such as the USA or Europe, in case they can be sold for very high prices and hence make a large profit for the criminal.

Consumption of the fake drug by the patient could result either in absence of therapeutic effect, or in complications up to fatality from wrong dosing/ingredients, or in case of under dosing in the development of new forms of viruses, tolerant to this type of drug. The latest is particularly dangerous as possible source of epidemical spread of viral infections.

It would accordingly be desirable to provide a means to check drugs in packaging that detects, not merely low end fakes, but also those intermediate level and high end fakes that do not exactly reproduce the genuine pharmaceutical product.

Traditional X-ray diffraction experiments for pharmaceutical substances are known. Firstly, the sample is prepared as a flat powder layer. This involves milling the drug and careful preloading to a flat surface for reflection geometry or between two transparent foils in transmission geometry, taking care of position and thickness.

Then, the sample is accurately aligned in the diffractometer within a beam path, and measurements and analysis are carried out.

The analysis becomes much more difficult when the substance is not available in the form of the powder, but preformed as solid tablet, often having curved shape. The special optical setup and geometrical arrangement is required in such case to obtain reasonable quality of data. Examples of such setups are "Advanced XRPD System for the Characterization of Pharmaceutical Compounds", V. Kogan, D. Beckers, PPXRD, 2006; "PXRD for nondestructive characterization of solid dosage forms", V. Kogan, D. Beckers, T. Degen, PPXRD, 2007; and "Characterization of formulations and drug products by PXRD", V. Kogan, D. Beckers, J. Nicolich, IWPCPS, 2007.

This type of experiment requires the direct access to the tablet and possibility for careful alignment of the goniometer axes with the sample.

It will be readily appreciated that such a process is not possible without removing the drug from packaging. Indeed, without removing the dosage form from the packaging, the dosage form is not fixed inside the packaging so even accurate alignment is a major problem, let alone preparing a sample of the exact required thickness.

Recently, there has been proposed an EDXRD system for scanning packaged pharmaceutical products. Little technical information about this system is available to the applicants.

However, EDXRD systems have difficulties associated with them and in particular they are not well suited to determining the phase of components of the drug dosage forms. Moreover, their angular resolution is limited relatively angle dispersive XRD systems as well as significantly higher background level. The difference is particularly strong for registration of large d-spacings (low 2θ range in angle dispersive XRD) usually used for characterization of pharmaceuticals. They are therefore not well suited to distinguishing relatively sophisticated fake drugs, such as intermediate level or high-end fakes, from genuine products. They can also be less capable in detecting amorphous materials, which may be used quite commonly in pharmaceutical dosage forms.

SUMMARY OF INVENTION

According to the invention there is provided an apparatus according to claim 1.

By aligning the measurement system with a predetermined part of the dosage form, good X-ray diffraction measurements can be obtained. Results are presented below showing how significant this is.

The choice of X-ray optics with a convergent and/or parallel beam improves measurement in the case that the dosage form is not exactly aligned, in the case the beam penetrates through the thick part of tablet in transmission geometry and in the case of curved tablet surface in reflection geometry. Unlike prior art EDXRD systems, which measure X-rays as a function of energy, the invention uses X-rays as a function of angle as the measured X-ray signature, i.e. angle-dispersive X-ray diffraction.

In order to achieve good resolution and reproducibility of results against the reference in spite of being unable to exactly align the dosage form which may be loose inside the packaging, or indeed to choose the optimal thickness of the sample for measurement, the apparatus includes a controller for aligning at least one predetermined part of the dosage form with the measurement system for measurement. The choice of predetermined part for each pharmaceutical product may be stored in the data library together with data and the individual procedure for each type of product.

Importantly, XRD provides direct fingerprint of complex properties of substance inside tablet while other counterfeit measures like RFID technology, coded labelling, bar codes are only addressing the additions to the drug product that is difficult to reproduce.

BRIEF DESCRIPTION OF DRAWINGS

Embodiments of the invention will now be described, purely by way of example, with reference to the accompanying drawings, in which.

The same or similar components are given the same reference numerals in the different figures. The drawings are schematic and not to scale.

DETAILED DESCRIPTION

A measurement system and method according to a first embodiment will be described with reference to FIGS. 1 to 5.

Figure 1:
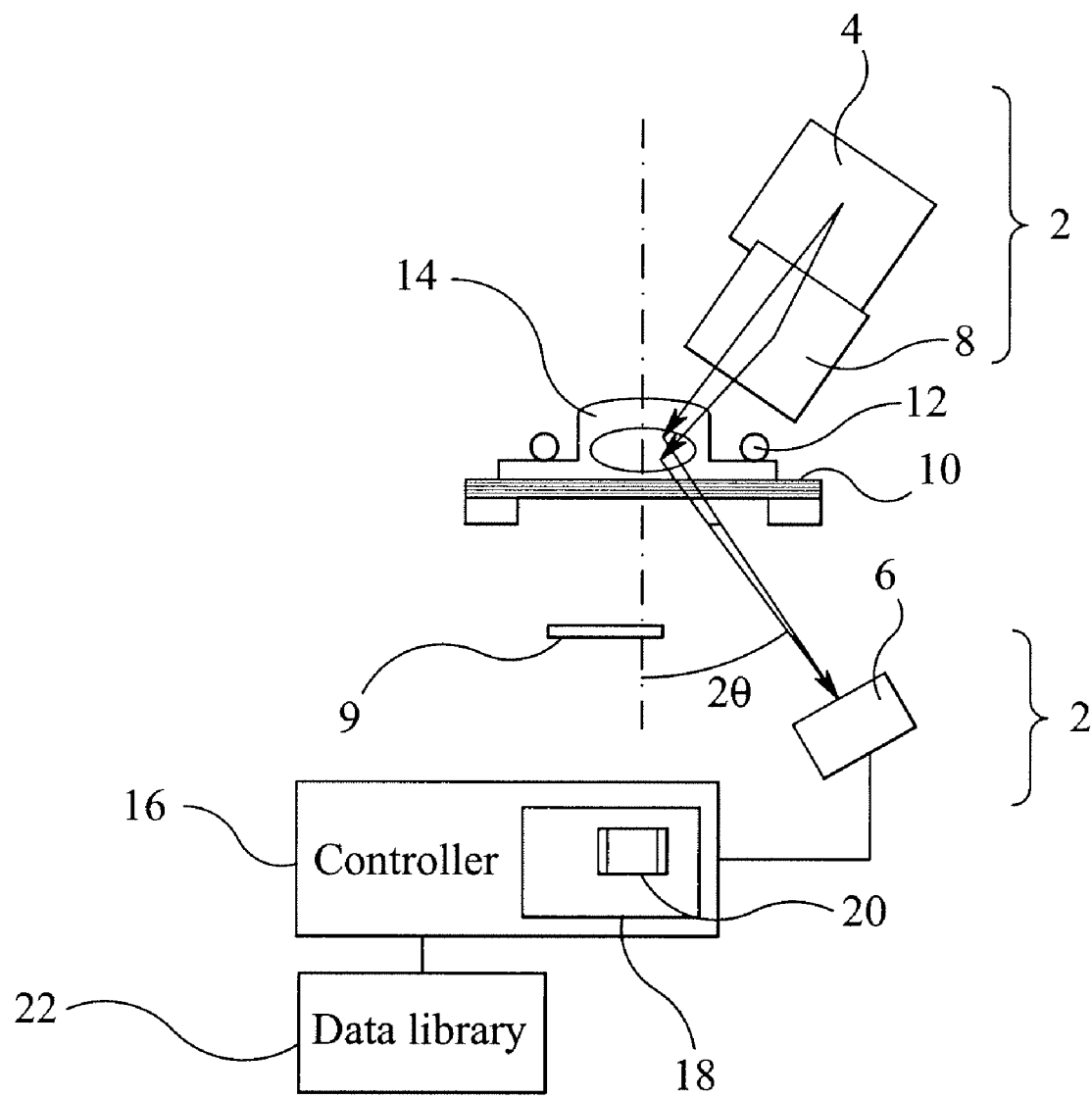
FIG. 1 shows apparatus according to a first embodiment of the invention.

Referring to FIG. 1, a measurement system 2 includes an X-ray source 4, an X-ray detector 6, and X-ray optics 8. In the specific embodiment, the X-ray optics 6 are a beam conditioner producing a convergent X-ray beam. The X-ray source 4 and X-ray detector 6 are mounted on independent goniometer for relative motion about the central sample position. The X-ray optics 8 are mounted on the same goniometer as the X-ray source 4. A beam stop 9 is used for some measurement configurations.

A sample holder 12 mounted on an X-ray table 10 which can be moved vertically (the z direction) and horizontally in x and y directions, is used to mount a sample 14 in use. The sample is intended to be a pharmaceutical product including a dosage form in packaging.

A computer 16 is provided, with a computer program product 18 stored in memory 20. The computer 16 acts as a controller to control the measurement system and X-ray table to carry out measurements. The computer program product acts to cause the computer 16 to carry out methods as set out in further detail below. The computer 16 also acts as comparison means for carrying out a comparison of the measured results.

A data library 22 is provided, containing data regarding a number of pharmaceutical products. The data library 22 is shown separately, but may of course be included within computer 16. The data includes X-ray signatures, as well as data giving optimal measurement positions on the dosage forms and procedural details.

Figure 2:
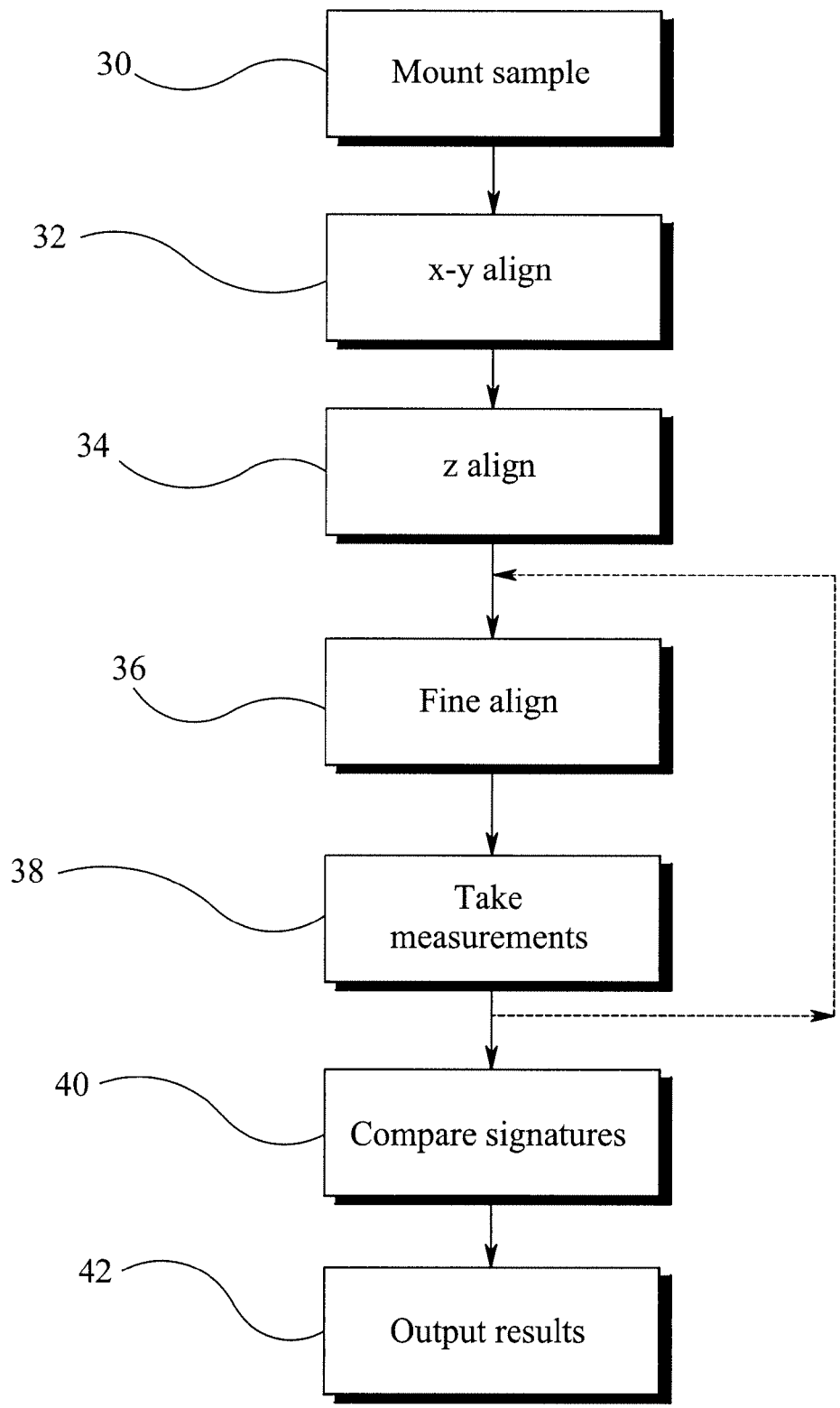
FIG. 2 shows a flow chart of a first embodiment of a method according to the invention.

In use, with reference to flow chart of FIG. 2, a sample 14 in the form of a blister pack containing a drug dosage form is held by the sample holder 12 on X-ray table 10 (step 30).

Next, preliminary x-y alignment takes place (step 32). The X-ray source 4, X-ray optics 8 and X-ray detector are moved into a vertical alignment, i.e. a zero scattering angle position, and an X-ray beam is transmitted essentially vertically through the sample 14.

Figure 3:
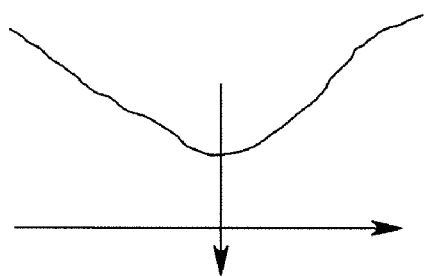
FIG. 3 shows measurements taken during an alignment stage.
Figure 4:
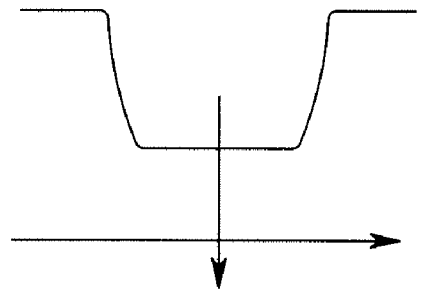
FIG. 4 shows measurements taken during an alignment stage for a different sample.

The X-ray table is moved in the x and y directions and the direct beam intensity measured as a function of position. Possible results are shown in FIG. 3 and FIG. 4. FIG. 3 shows the results measured on a thin curved tablet transparent for x-rays and FIG. 4 the results from a large tablet not transparent for x-rays in the central part. The X-ray table is then positioned for optimal measurement. In the thin curved tablet example (FIG. 3) the optimal position is the centre of the tablet. For the larger tablet of FIG. 4 a region close to the edge is chosen.

In alternative embodiments, preliminary x-y orientation is obtained using an optical camera, which is particularly useful in the case of transparent blisters.

The next step is to carry out the vertical alignment, i.e. in the z-direction (step 34).

An example will be given where the packaging is a blister package and the dosage form a tablet.

A first approach is to obtain a model of the blister cavity and tablet shape, which may conveniently be stored in data library 22, and use this to align the X-ray table correctly in the z direction.

The mathematical procedure followed may be firstly to define the outer surface of the dosage form in Cartesian coordinates as $z_{tab}$=tablet (x,y) where tablet( ) is the function defining the form. The form of the blister cavity may be similarly defined as $z_{blister}$=blister (x,y), where blister ( ) is the function defining the form of the blister in the same coordinates. In both cases, the table 12 is set at the zero vertical position z=0.

The force of gravity is assumed to be vertically down.

The correct height z of the table may then by found by function z=abs(tablet(x,y)−blister(x,y)) taken at x,y of intersection of two surfaces.

Figure 5:
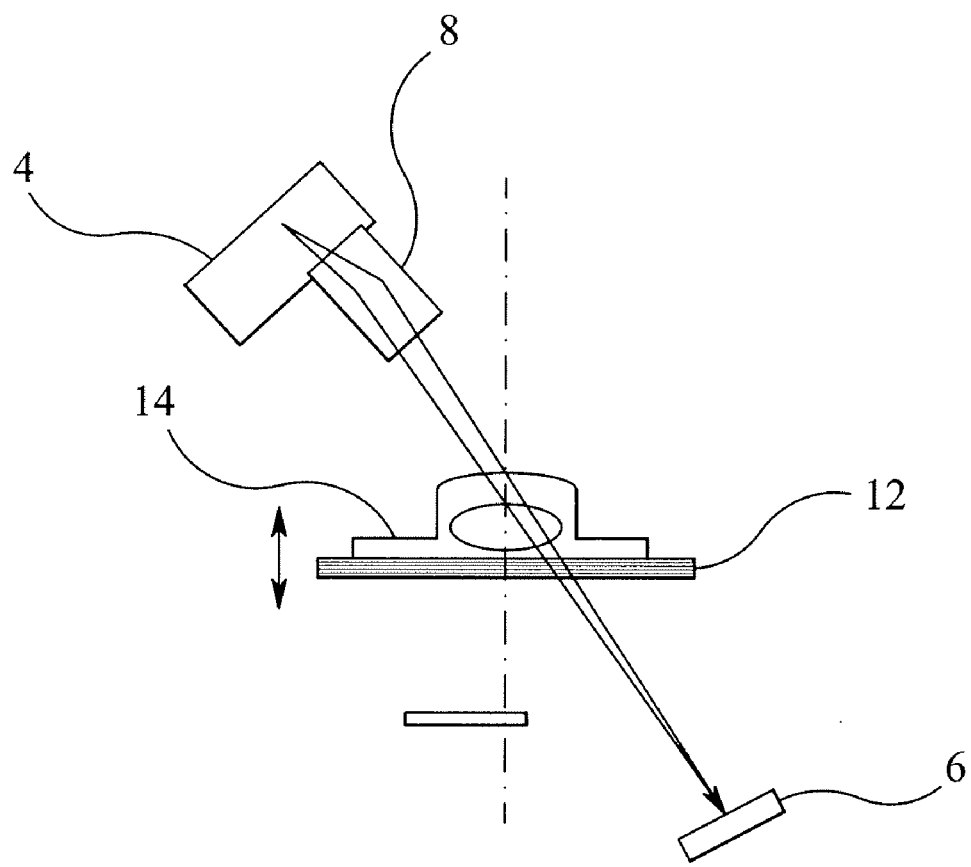
FIG. 5 illustrates a configuration for vertical alignment.

An alternative approach is to move the X-ray source 4, X-ray optics 8 and detector 6 to the position shown in FIG. 5 where both source 4 and detector 6 are in a direct line, but at an angle θ to the vertical. Then, the table 12 is moved vertically (in the z-direction) and a similar measurement of absorption against position made as in the x-y alignment.

The optimum alignment of the dosage form is then chosen, either the position of maximum absorption or the centre of the flat absorption.

In the next step, further adjustment is carried out (step 36) if required.

Absorption of x-rays entering a thin layer with thickness t (as coating or blister wall) under the incidence angle α is typically expressed as $$I = I_0 \exp\left(\frac{\mu t}{\cos()}\right)$$

where μ is a linear absorption coefficient of material

The previous steps align the centre of the dosage form with the centre of the measurement equipment. However, the optimal position of a tablet or other dosage form depends on the dosage form, and in particular the thickness of the dosage form. The optimal thickness for measurements in transmission geometry is normally given by $\mu.t \sim 1$, so exponent(m.t) ~e, where e is the numeric constant (about 2.7), μ the linear absorption coefficient and t the thickness.

Thus, optimal measurement requires that 50% to 80% of X-rays are absorbed, and tablets thicker than 3 mm may well absorb more than this, depending on the material. Accordingly, for thicker tablets, the table 12 may be moved to the optimal position for a particular tablet, which may for larger tablets be away from the central position.

The chosen specific location of the dosage forms for measurement takes into consideration a number of factors. The exact choice of alignment will depend on the pharmaceutical product and is recorded for each pharmaceutical product in library 22. Some considerations for the best choice of alignment are as follows.

For actual measuring of tablets in a blister, we are dealing with complex absorption factors incorporating absorption in the interior of the tablet, from the API and excipient, absorption in the tablet coating and absorption in the blister. All factors are dependent on the position of the incident X-ray beam and the emerging X-ray beam relative to the blister and tablet, orientation of the tablet and orientation of blister walls.

The coating of the tablet may contain highly absorbing (versus organic) substances and the material of blister wall may be typically either polymer or metal (aluminium) with perhaps inclined walls making the beam path in the metal foil quite long and absorption significant.

The fact that the thickness of tablets inside the packaging may not be changed is a serious obstacle to make system generally applicable to broad range of pharmaceutical products. Instead, therefore, the system must take measurements at the correct location to minimise negative effects of a suboptimal thickness.

The dosage form is not fixed inside the packaging and generally its actual position is unknown. The alignment processes used ensures sufficient alignment for good angle-dispersive X-ray diffraction measurements.

Since the shape of the tablets or other dosage forms is often convex the measurements are dependent on area where the incident beam hit the tablet.

In conclusion, therefore, the alignment chosen for each pharmaceutical product takes account of the known absorption profile of the dosage form within the absorption profile of complete packaging perhaps containing strongly absorbing areas. This information may be used for alignment, for check of correct orientation (no tilts) and for measurement of dimensions.

A further factor that is relevant for alignment is orientation of the dosage forms. Often, the best orientation is through the shortest path through the sample as providing best possible resolution. For a flat dosage form, such as a flat tablet, the best orientation may be with the tablet flat and the X-rays essentially vertical. In contrast, for a cylinder-shaped dosage form, the cylinder should be horizontal and the X-rays vertically across the cylinder.

If the blister pack is mounted flat, it will not normally be possible to further adjust the orientation of the dosage form. Normally, a vertical alignment of X-ray source 4 and detector 6 will give the correct results, but in some cases the optimal orientation of X-ray beam will be obtained with a horizontal beam, or even some other angle.

In still further embodiments, or for particular pharmaceutical products, the blister pack may be mounted vertically so that the dosage form falls under gravity to rest on the edge of the blister cavity. In this way, the position of the dosage form may be more accurately known within the packaging which can improve the results.

It is an important feature that the analysis is taken on specific positions of the dosage form since this greatly eases comparison with the stored drug signatures, as well as allowing more accurate measurement.

Since the optimal position depends on the particular pharmaceutical product, the movement to the optimal position (step 36) requires prior knowledge of the pharmaceutical product to be tested. This will normally be the pharmaceutical product indicated on the product packaging.

For some applications, the pharmaceutical product may not be known. In this case, an iterative procedure may be adopted, by carrying out the following steps to get a first approximation to the identity of the sample, and then returning to step 36 to optimise the position to repeat the measurements at the optimal position.

An alternative approach is to take measurements at multiple positions, and to determine the optimal one of the measurements by comparison with the X-ray signatures after taking the measurements.

A number of these approaches may be used together. Further alignment techniques are described below with reference to the second embodiment, and these may be combined with those of the first embodiment.

The embodiment thus includes alignment to align the tablet in the blister packaging with a predetermined alignment to make the signatures measured readily comparable to those stored in the library.

With alignment completed, measurement may take place (step 38). Note that the alignment and measurement steps 36, 38 may be repeated to take multiple measurements, as indicated by the dotted arrows in FIG. 2.

Dosage forms are not in general flat, and have curved surfaces. In order to obtain better results on amorphous samples with curved surfaces, a particular geometry is adopted. That geometry is a transmission geometry, using a convergent beam focused on the detector.

Typically, relatively small angles 2θ will be used, up to 15-20°, or up to 40° when using Cu Kα radiation.

It is a particular feature of this embodiment that a convergent line geometry is used in which the optics 8 focus the beam on a line, in the plane of the paper as shown in FIG. 1. This provides good resolution and sufficient speed.

In a preferred implementation, the beam size of the X-rays at the sample measured in the direction transverse to the X-beam can be made 0.2 mm or less, preferably 0.1 mm or less. In this way, accurate positions and dimensions on the sample can be taken.

In a particular embodiment, a small angle transmission geometry is used. The X-ray source 4 and optics 8 are arranged to supply convergent X-rays, focused on the detector 6. The beam stop 9 is used to stop the direct beam, and the detector position varied on its goniometer to measure X-rays as a function of angle.

Figure 6:
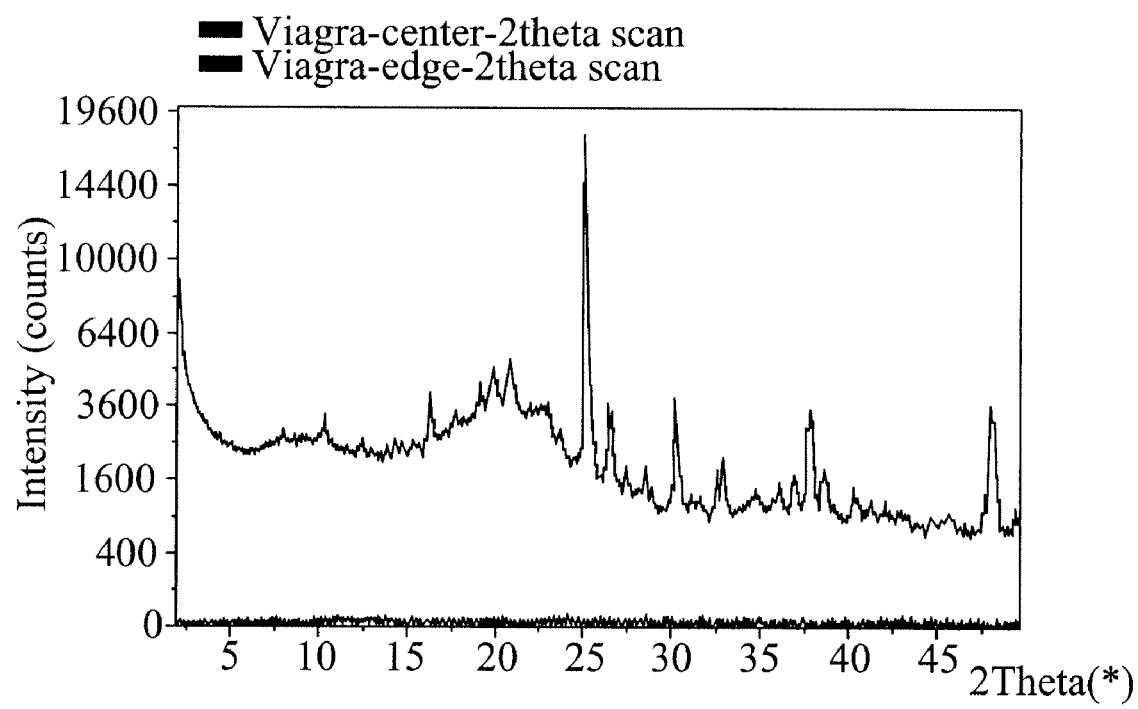
FIG. 6 illustrates results taken using the invention.

Some measured results are presented in FIG. 6. This represents a Levitra tablet in a blister.

Figure 6A:
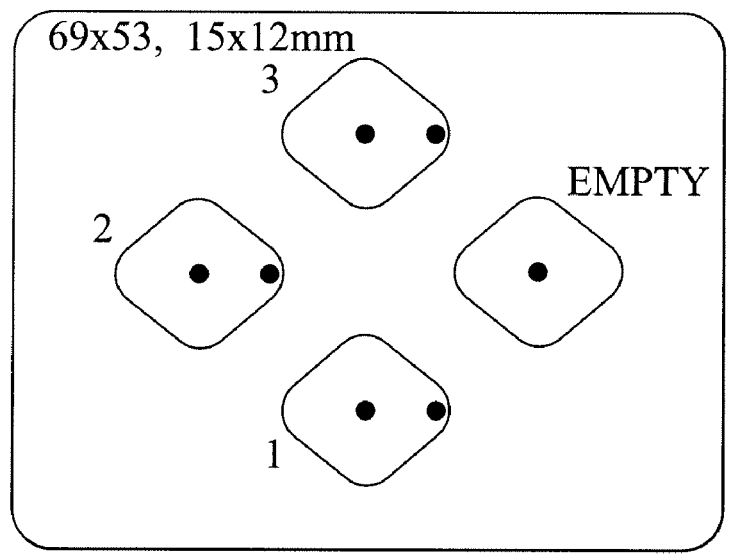

FIG. 6 shows in particular measurements made at the centre of a thicker tablet (lower curve) and towards the edge (upper curve). It will be seen that the lower curve provides no useful information and is essentially pure noise. This demonstrates the importance of choosing the correct position. FIG. 6a shows the measurement positions, the central position and the edge position for each of three tablets.

Figure 7:
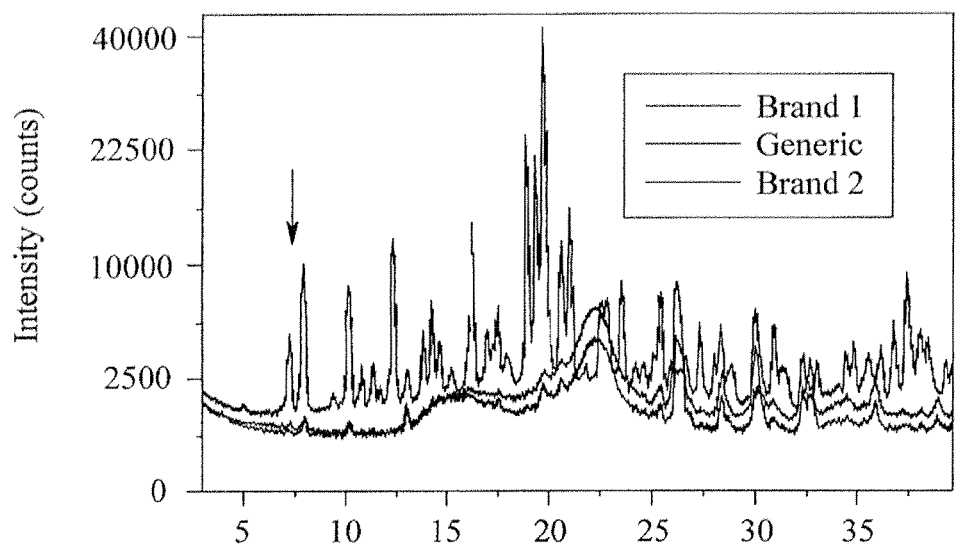
FIG. 7 illustrates X-ray powder diffraction results taken using the invention.

In a particular implementation, and for certain pharmaceutical drugs, the X-ray signature is an X-ray powder diffraction (XRPD) pattern. FIG. 7 illustrates the X-ray powder diffraction pattern for two genuine drug products, including the same drug but formulated in different countries, and one fake drug product of the similar brands.

The peaks are much larger for the fake drug product than for the genuine product. The peaks from the API are indicated with an arrow, showing that the genuine product has amorphous API but the fake product crystalline API. The use of XRPD allows the peaks to be seen in both genuine and fake products, and a clear distinction to be made between the genuine and fake products.

At low angles (values of 2θ below about 12°), contributions from the API are seen. Contributions from the blister pack are seen as specific peaks at higher angles, for example above 25°.

In the tested example, the same applies to the excipients which gives rise to peaks at higher angles. Again, in the example the excipients is highly crystalline in the fake product.

Alternatively or additionally, small angle X-ray scattering (SAXS) measurements may be used as the X-ray signature.

Figure 8:
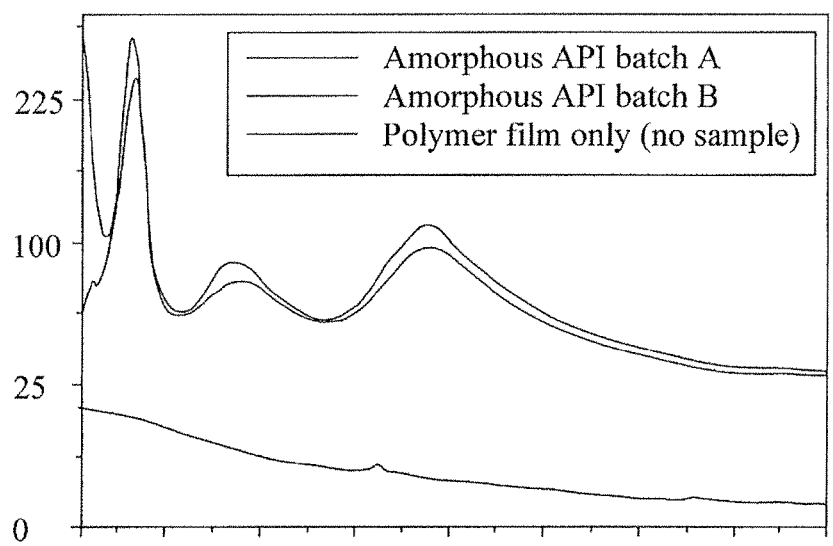
FIG. 8 illustrates small angle X-ray scattering results.

FIG. 8 shows two X-ray diffraction patterns measured at very low angles for two batches of API. The two batches appear alike except at the very lowest scattering angles, where there is a peak for one batch and not the other. This results from the different technological processes used to manufacture the two batches. Thus, the use of SAXS allows determination of fakes, even high-end fakes using a very similar amorphous API to the amorphous API in the genuine product.

Please note that the measurements of FIG. 8 are by way of illustration since they are not in fact measured with a blister pack present. However, the addition of a blister pack is not expected to change the fundamental situation at low angles. Instead, more peaks at higher angles would be added.

One issue that can occur when taking measurements of tablets in blisters is a poor particle statistics and texture. The reflections from substances with large crystallites may exhibit strongly distorted, spiky patterns versus the measurements.

To deal with this issue multiple repetitive measurements may be made on different parts of the same tablet and on different tablets with subsequent summation and averaging before comparing the measured signatures with reference signatures.

Figure 10:
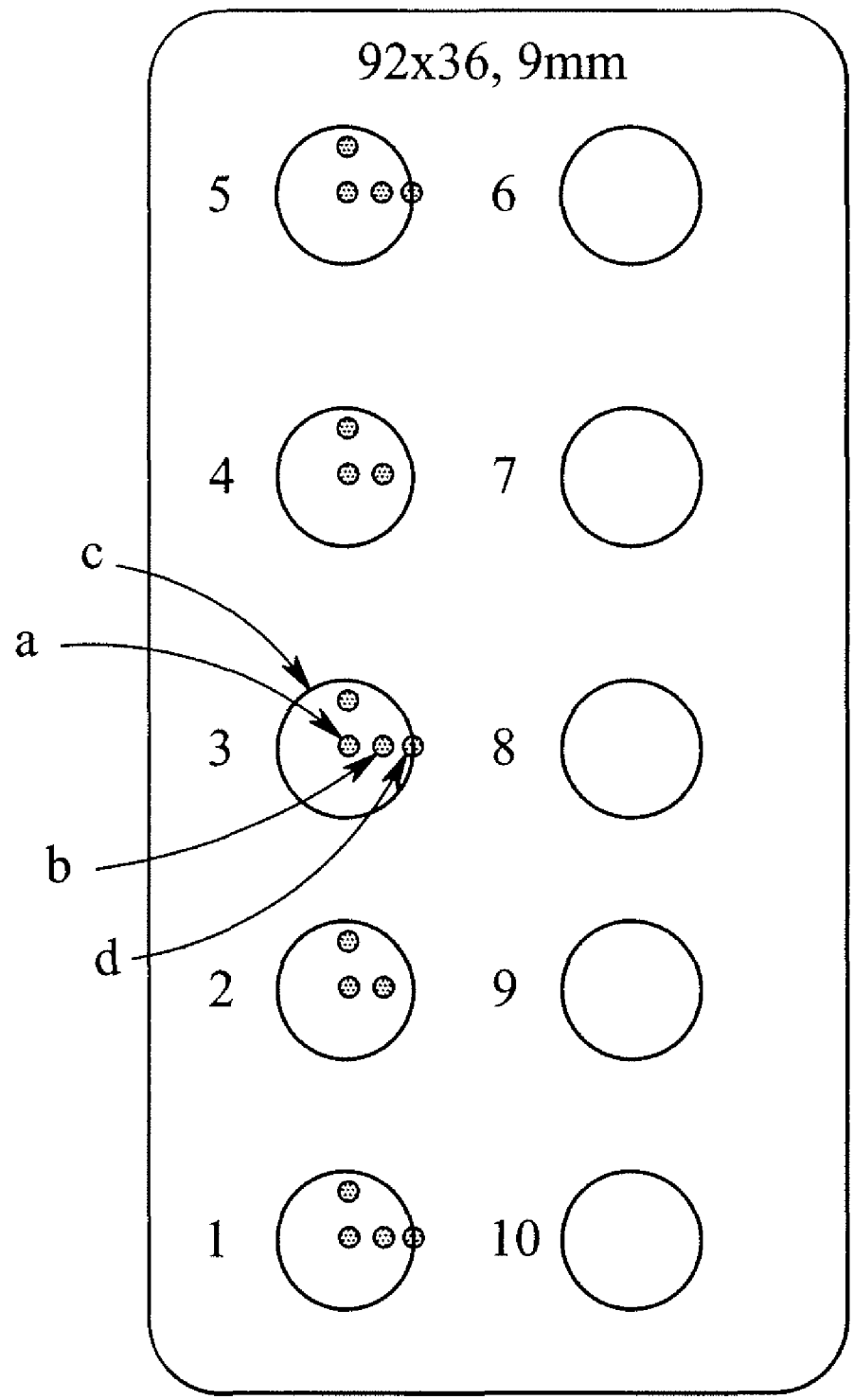
FIG. 10 illustrates measurement positions.

FIG. 10 illustrates measurement positions for a blister, of Valium (R), that may be used. The dots show the measurement positions.

An enhancement that may be used is to shake or move the table to adjust the position of the pharmaceutical inside the packaging, and then repeat the measurements. In this way, multiple measurements can be taken. The final results can then be averaged to reduce effects of particular artefacts in one position.

A further point of note is that the convergent line geometry of the X-ray beam with focusing on the sample allows both transmission and reflection measurements to be taken. The same apparatus can be used to take reflection measurements simply by moving the detector 6 to be on the same side of the sample as the source 4 or rotating the sample surface 90 degrees.

The small spot can be used to probe the size of the pharmaceutical by moving the sample in the x-y plane and measuring the absorption. The size of the sample can be used as a measured signature and this can be compared with the known size of the pharmaceutical as the reference signature.

Another signature that may be measured is the absorption of the sample in the direct beam position, where the X-ray beam passes un-diffracted through the sample.

The first embodiment uses X-ray signatures with direct beam transmission coefficients, small angle X-ray scattering, or both, to obtain measurements of amorphous materials. Direct beam transmission measurements are particularly reliable with two X-ray energies, since this allows two measurements to be made and hence the measurements are much more reliable. The type(s) of measurement suitable for each pharmaceutical product is stored in library 22, together with reference X-ray signatures captured in the same way.

The reference signatures need not be obtained from measurements in packaging. They may be obtained from the dosage form, the dosage form turned to powder, the dosage form core, the coating alone, the packaging alone, the dosage form in the packaging, the API in pure form, a placebo, and a placebo without the API. Indeed, preferably, multiple such reference signatures are used in order to detect fakes more readily.

The reference signatures may also be obtained after heating which can recrystallise amorphous APIs and hence make peaks more apparent. Further, if the API in the product is in a particular state, this can be obtained before measurements.

The measured signatures are compared with reference signatures stored in the library 22 (step 40).

In a preferred implementation, a number of different measured signatures are compared with reference signatures. The measured signatures may include SAXS measurements, XRPD, geometric dimensions of the pharmaceutical, absorption, as well as measurements of the packaging alone. The use of multiple parameters improves accuracy.

The end result of these comparisons is a output result (step 42) that may typically be simply green, to indicate a good match of the measurements with the reference, red, to indicate a fake, and amber, to indicate uncertainty. Such simple outputs are convenient in a real world application when the equipment is operated by less-trained personnel.

In a second embodiment, two X-ray energies are used, that is hard X-rays and soft X-rays. This allows the use of the system for both thick and thin tablets, and also allows the system to be used with other pharmaceutical products such as products in glass bottles.

In this case, the higher energy (hard) X-rays will still penetrate thicker tablets, bottles and jars. Even with thinner tablets, the two X-ray signatures at different energies can give improved discrimination.

The use of two X-ray energies is particularly important when measuring samples with amorphous APIs which may give only very small peaks.

A third embodiment allows more precise alignment of blister packets.

In step 32, for the alignment of the tablet in the blister package to the suitable measurement position, first the positions of the tablet in the blister are determined by x, y scans of the blister pack using the direct vertical beam with both source and detector oriented vertically.

Figure 9:
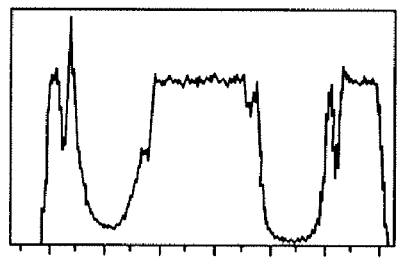
FIG. 9 illustrates a second embodiment of the invention.
Figure 9:
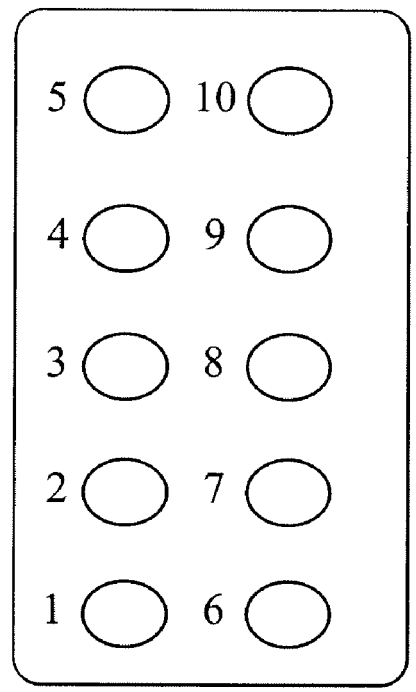
Figure 9:
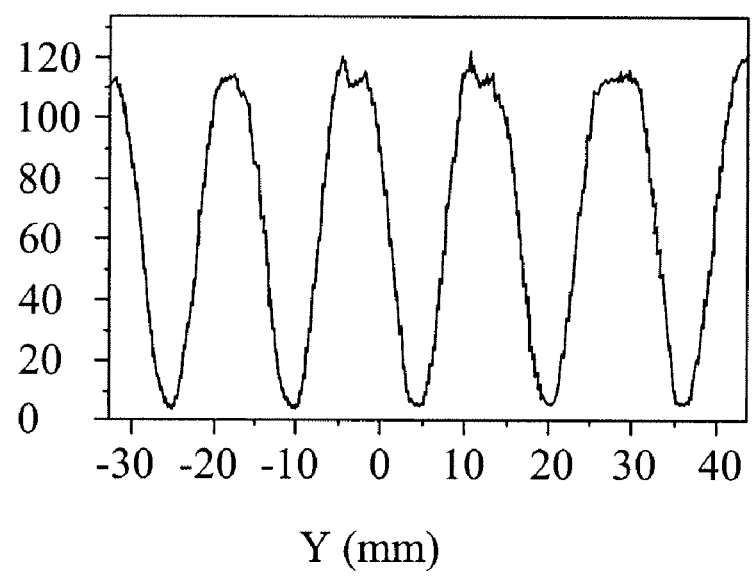

FIG. 9 shows an example of a blister pack and typical scans recorded in the direct beam. The recorded pattern can be used to position a tablet into the direct beam (in the x-y direction). The z alignment (step 34) is then carried out.

Then, a plurality of measurements are made at a plurality of further fine positions, in essence repeating steps 36 and 38. For the further positioning of the sample information from the database about the sample positioning strategy is needed. The database contains a strategy how to position the tablet to collect the set of representative signatures for evaluation.

In this embodiment, a set of scans collected at different x-y positions or even also different z positions is recorded. The set of measured scans is then compared with the stored signatures from the library 22.

In a fourth embodiment, a more accurate alignment of the tablet using reflections is used after the preliminary alignment set out above.

In this case, reference signature information from the database is used. The reference signature information includes information about a characteristic feature in the signature, such as a strong reflection. The goniometer is positioned with a source at angle θ and detector at angle 2θ wherein θ is the angle of the characteristic feature in the signature (e.g. a strong reflection). Then the table 10 is adjusted in the x and y directions to maximise the intensity of this peak.

Z-positioning is then done afterwards (keeping θ at zero) by comparing a measured 2θ-z map with information from a previously collected signature in the database.

A fifth embodiment takes any of the above embodiments and uses a position sensitive detector 6. This can allow faster measurements or improved measurements.

In a sixth embodiment a different alignment technique is used for the z direction (step 34). In the alternative alignment technique, the x-y alignment is carried out as above. Then, the system is brought into a measurement position and a known peak at a known angle 2θ is taken from the library 22. The known peak used for alignment is preferably a strong peak.

Then, the detector 6 is positioned at the correct angle for the known peak and the holder 10 moved in the z direction until the detector 6 picks up the correct maximum value. In this way, the correct vertical orientation is achieved.

It will be appreciated by those skilled in the art that the above embodiments are by way of example only and many modifications are possible.

For example, although the above embodiments describe the use of a transmission geometry, it may in alternative embodiments be appropriate to use a reflection geometry.

The pharmaceutical packaging is not restricted to blisters, but plastic bags, vials, bottles and jars are also possible.

The pharmaceuticals may be in powder form inside the packaging.

The X-rays may be used to identify hidden bar codes, signs, signatures and the like.

The X-ray optics 8 may use a multi-layered structure, a poly-capillary optic, or a crystal monochromator.

The dosage form (pharmaceutical) may be a solid, liquid, granules or loose powder.

The invention claimed is:

1. A system for checking pharmaceutical products including a pharmaceutical dosage form inside packaging, comprising:

a measurement system having an X-ray source for generating X-rays, X-ray optics, and an X-ray detector for detection of X-rays to obtain a measured X-ray signature;

a holder for carrying the packaging with the dosage form inside for measurement by the measurement system;

a data library containing one or more reference X-ray signatures for at least one pharmaceutical product, wherein the data library includes data giving at least one predetermined location on the dosage form for at least one respective pharmaceutical product; and a comparison means for comparing a measured X-ray signature with the reference X-ray signatures;

wherein:

the X-ray optics are arranged to create a convergent and/or parallel beam;

the X-ray detector is mounted on a goniometer for detection of X-rays as a function of angle as the measured X-ray signature; and further comprising a controller for driving the holder to align the predetermined location on the dosage form with the measurement system for measurement.

2. A system according to claim 1, wherein the X-ray source generates X-rays at a plurality of characteristic wavelengths and wherein the library includes respective reference X-ray signatures at the characteristic wavelengths.

3. A system according to claim 1, wherein:

the controller is arranged to control the holder to capture a plurality of measured X-ray signatures at a plurality of predetermined locations on of dosage form and measurement system; and the comparison means is arranged to compare the measured X-ray signatures with a plurality of reference X-ray signatures.

4. A system according to claim 1, wherein the controller is arranged to control the holder to capture a plurality of measured X-ray signatures of different type; and the comparison means is arranged to compare the measured X-ray signatures with a plurality of reference X-ray signatures.

5. A system according to claim 1, wherein the controller is arranged to control the holder to capture measurements of X-ray absorption as a function of horizontal position of the holder and to align the holder to align at least one predetermined location on the dosage form with the measurement system from the captured measurements of X-ray absorption as a function of position.

6. A system according to claim 1, wherein the controller is arranged to control the holder to capture measurements of X-ray absorption as a function of horizontal position of the holder and to align the holder to align at least one predetermined location on the dosage form with the measurement system from the captured measurements of X-ray absorption as a function of position.

7. A system according to claim 1, wherein the reference signatures stored in the library include a plurality of reference signatures relating to the active pharmaceutical ingredient, the excipient, the coating or the packaging separately or combined.

8. A system according to claim 1, wherein the controller is arranged to align the holder horizontally, then vertically, and then to align the dosage form in the at least one predetermined location.

9. A system according to claim 1, wherein the X-ray optics are arranged to focus the X-ray beam on the X-ray detector to measure the X-ray signature in a transmission geometry.

10. A system according to claim 1 wherein the X-ray detector is a pixel detector measuring X-rays as a function of position.

11. A system according to claim 1 wherein the X-ray signatures include X-ray powder diffraction signatures.

12. A system according to claim 1 wherein the X-ray signatures include Small Angle X-ray scattering signatures.

13. A system according to claim 1 wherein the X-ray signatures include the geometrical dimensions of the dosage form.

14. A system according to claim 1 wherein the X-ray signatures include the RAMAN spectrum.

15. A method for checking pharmaceutical products including a pharmaceutical dosage form inside packaging, comprising:
   mounting a pharmaceutical product on a holder;
   aligning the pharmaceutical product with a measurement system having an X-ray source for generating X-rays, X-ray optics, and an X-ray detector for detection of X-rays;
   obtaining information specifying a specific part of the pharmaceutical from a library, wherein the data library includes data relating the respective specific parts of the pharmaceutical for respective pharmaceutical products;
   measuring an X-ray signature on the specific part of the pharmaceutical as a function of diffraction angle; and
   comparing the measured X-ray signature with reference X-ray signatures.

16. A method according to claim 15 including positioning the pharmaceutical in a particular location inside the packaging cavity before taking measurements.

17. A method according to claim 15 including measuring a plurality of X-ray signatures on a plurality of different specific parts of the pharmaceutical as a function of diffraction angle.

18. A method according to claim 15 further comprising aligning the pharmaceutical so that the X-ray beam takes the shortest path through the sample from side to side.

* * * * *

UNITED STATES PATENT AND TRADEMARK OFFICE
CERTIFICATE OF CORRECTION

PATENT NO. : 7,756,248 B2
APPLICATION NO. : 12/370540
DATED : July 13, 2010
INVENTOR(S) : Vladimir Kogan et al.

Page 1 of 1

It is certified that error appears in the above-identified patent and that said Letters Patent is hereby corrected as shown below:

On the Title Page, in Item [75], under Inventors, at line 6, delete "Cologne" and insert --Koln--.

Signed and Sealed this
Twelfth Day of July, 2011

David J. Kappos
*Director of the United States Patent and Trademark Office*